US012599492B2

(12) United States Patent
Ding et al.

(10) Patent No.: US 12,599,492 B2
(45) Date of Patent: Apr. 14, 2026

(54) AXIALLY COMPRESSIBLE BARE STENT

(71) Applicant: SHANGHAI FLOWDYNAMICS MEDICAL TECHNOLOGY CO., LTD., Shanghai (CN)

(72) Inventors: Jian Ding, Shanghai (CN); Chenying Fan, Shanghai (CN)

(73) Assignee: SHANGHAI FLOWDYNAMICS MEDICAL TECHNOLOGY CO., LTD., Shanghai (CN)

( * ) Notice: Subject to any disclaimer, the term of this patent is extended or adjusted under 35 U.S.C. 154(b) by 666 days.

(21) Appl. No.: 18/003,357

(22) PCT Filed: Nov. 6, 2020

(86) PCT No.: PCT/CN2020/127259
§ 371 (c)(1),
(2) Date: Dec. 27, 2022

(87) PCT Pub. No.: WO2022/007280
PCT Pub. Date: Jan. 13, 2022

(65) Prior Publication Data
US 2023/0240867 A1      Aug. 3, 2023

(30) Foreign Application Priority Data

Jul. 6, 2020      (CN) .......................... 202010643320.4

(51) Int. Cl.
*A61F 2/90* (2013.01)
*A61F 2/86* (2013.01)
*A61F 2/82* (2013.01)
(52) U.S. Cl.
CPC .................. *A61F 2/90* (2013.01); *A61F 2/86* (2013.01); *A61F 2002/823* (2013.01)

(58) Field of Classification Search
CPC ...... A61F 2/04; A61F 2/82; A61F 2/86; A61F 2/88; A61F 2/885; A61F 2/90; A61F 2/07;
(Continued)

(56) References Cited

U.S. PATENT DOCUMENTS 6,015,432 A     1/2000   Rakos
6,592,617 B2    7/2003   Thompson
(Continued)

FOREIGN PATENT DOCUMENTS

CN          1479597 A        3/2004
CN        102727332 A       10/2012
(Continued)

OTHER PUBLICATIONS

Supplementary European Search Report in the European application No. 20944499.1, mailed on Jul. 5, 2024. 7 pages.
(Continued)

*Primary Examiner* — Dinah Baria
(74) *Attorney, Agent, or Firm* — Syncoda LLC; Feng Ma

(57) ABSTRACT

An axially compressible bare stent for an aorta, formed by interleaving at least two wires having different diameters, i.e., a first wire and a second wire, in an overlapping manner. In a natural release state, the bare stent has a metal coverage of at least 30%. The first wire has a diameter of 20-150 μm, and the second wire has a diameter of 150-600 μm. During the use in the treatment of aortic aneurysms and/or aortic dissection lesions, low liquid permeability and a strong radial support force are provided at a desired location in an aorta by means of the axial compressibility of the bare stent.

16 Claims, 7 Drawing Sheets

(58) Field of Classification Search

CPC ....... A61F 2250/0039; A61F 2002/823; A61B 17/12113

See application file for complete search history.

(56) References Cited

U.S. PATENT DOCUMENTS

| | | | |
|---|---|---|---|
| 7,052,513 B2 | 5/2006 | Thompson | |
| 7,588,597 B2 | 9/2009 | Frid | |
| 9,655,710 B2 | 5/2017 | Eller | |
| 10,470,904 B2 | 11/2019 | Folan | |
| 10,653,511 B2 | 5/2020 | Eller | |
| 10,653,512 B2 | 5/2020 | Eller | |
| 2001/0056299 A1 | 12/2001 | Thompson | |
| 2003/0100945 A1* | 5/2003 | Yodfat ..................... | A61F 2/82 623/1.53 |
| 2004/0073293 A1 | 4/2004 | Thompson | |
| 2004/0215332 A1 | 10/2004 | Frid | |
| 2006/0190070 A1 | 8/2006 | Dieck | |
| 2007/0168019 A1 | 7/2007 | Amplatz | |
| 2010/0161025 A1 | 6/2010 | Kuppurathanam | |
| 2013/0085565 A1 | 4/2013 | Eller | |
| 2014/0067047 A1 | 3/2014 | Eller et al. | |
| 2014/0248418 A1 | 9/2014 | Eller et al. | |
| 2014/0249619 A1 | 9/2014 | Eller et al. | |
| 2017/0100231 A1* | 4/2017 | Frid ........................ | A61F 2/852 |
| 2017/0333230 A1 | 11/2017 | Folan | |
| 2019/0223879 A1 | 7/2019 | Jayaraman | |
| 2020/0046528 A1 | 2/2020 | Folan | |
| 2020/0383767 A1 | 12/2020 | Eller et al. | |
| 2021/0137715 A1* | 5/2021 | Ringwala ............... | A61F 2/966 |

FOREIGN PATENT DOCUMENTS

| | | | |
|---|---|---|---|
| CN | 103561682 A | 2/2014 | |
| CN | 104042296 A | 9/2014 | |
| CN | 203885667 U | 10/2014 | |
| CN | 104689379 A | 6/2015 | |
| CN | 104720941 A | 6/2015 | |
| CN | 105125326 A | 12/2015 | |
| CN | 105228561 A | 1/2016 | |
| CN | 107106286 A | 8/2017 | |
| CN | 207400830 U | 5/2018 | |
| CN | 109890323 A | 6/2019 | |
| CN | 109966018 A | 7/2019 | |
| CN | 110013372 A | 7/2019 | |
| CN | 110234296 A | 9/2019 | |
| CN | 209347136 U | 9/2019 | |
| CN | 107427374 B | 10/2019 | |
| CN | 110353866 A | 10/2019 | |
| CN | 110731843 A | 1/2020 | |
| CN | 212662039 U | 3/2021 | |
| EP | 1946721 A1 | 7/2008 | |
| JP | H1033692 A | 2/1998 | |
| JP | H10328216 A | 12/1998 | |
| JP | 2004520101 A | 7/2004 | |
| JP | 2004528862 A | 9/2004 | |
| JP | 2012523922 A | 10/2012 | |
| JP | 2012223209 A | 11/2012 | |
| JP | 2017511742 A | 4/2017 | |
| JP | 2018000794 A | 1/2018 | |

OTHER PUBLICATIONS

International Search Report in the international application No. PCT/CN2020/127259, mailed on Apr. 2, 2021.

English translation of the Written Opinion of the International Search Authority in the international application No. PCT /CN2020/ 127259, mailed on Apr. 6, 2021.

Non-Final Office Action of the U.S. Appl. No. 18/003,891, issued on Oct. 1, 2025.

International Search Report in the international application No. PCT/CN2020/127273, mailed on Mar. 30, 2021.

Written Opinion of the International Search Authority in the international application No. PCT/CN2020/127273, mailed on Mar. 30, 2021.

Supplementary European Search Report in the European application No. 20943874.6, mailed on Jun. 24, 2024.

* cited by examiner

20

22

33a

33b

34

A                    B                    C

AXIALLY COMPRESSIBLE BARE STENT

CROSS-REFERENCE TO RELATED APPLICATIONS

This application is a National Stage of International Patent Application No. PCT/CN2020/127259 filed on Nov. 6, 2020, which claims priority to Chinese Patent Application No. 202010643320.4 filed on Jul. 6, 2020. The disclosures of the above-referenced applications are hereby incorporated by reference in their entirety.

TECHNICAL FIELD

The disclosure relates to a bare stent, and in particular to a bare stent for use in the treatment of aortic lesions, such as aortic aneurysms or aortic dissections.

BACKGROUND

A wall of an arterial blood vessel is composed of intima, tunica media and adventitia which are in tight contact with one other. When an inner wall of the arterial blood vessel is partially damaged, the tunica media of the wall of the arterial blood vessel is gradually peeled off under a strong impact of arterial blood flow, so that blood enters between the tunica media and the adventitia of the wall of the blood vessel to form two lumens, i.e., a true lumen and a false lumen. Aortic dissection is most commonly seen. The aortic dissection causes the arterial wall to become thin and weak, with a risk of rupture at any time. Once the dissection is ruptured, the patient will die in several minutes.

The aortic dissection is divided into two types, i.e., type A and type B (i.e., Stanford typing) according to a tearing site and an extension range of the intima. Type A refers to a lesion involving an ascending aorta, and a peeling site of the arterial wall starts from the ascending aorta, and may also occur at a proximal end of an aortic arch or of a descending aorta but involves the ascending aorta. Type B means that a peeling site of the arterial wall occurs at the descending aorta without exceeding a proximal end of an opening of a left subclavian artery.

The aortic aneurysm is also a disease of abnormal expansion of an aorta. Rupture of the aortic aneurysm is also fatal for the patient.

Therefore, it is very necessary to early diagnose and timely treat the aortic dissection and the aortic aneurysm.

At present, there are usually three solutions to treat the aortic dissection or the aortic aneurysm.

One solution is to use an open surgery for replacement of an artificial blood vessel. At present, this solution is mostly used in a type A aortic dissection, and has defects that an intraoperative mortality rate is high, a residual dissection (that is, a type B dissection is formed) is often formed after the surgery, and a proportion of requiring a surgery again within 10 years is up to 9% to 67%. Furthermore, this solution has a very high treatment cost, and relatively few hospitals have mastered this surgical technique. In addition, the open surgery is not suitable for all patients, and a very small proportion of patients may benefit from this solution.

Another solution is an EVAR intraluminal intervention method, i.e., a covered stent implantation. This solution has advantages of small trauma, fast recovery and low mortality rate. However, a site where a stent is placed often involves an aortic arch and/or an abdominal aorta, three branch artery blood vessels at a convex side of the aortic arch, and main branch artery blood vessels such as a left renal artery, a right renal artery, a coeliac trunk artery, a superior mesenteric artery, or the like at the abdominal aorta cannot be obstructed during the whole surgery and after the surgery. Conventional practice is to drill a hole at a site of the covered stent corresponding to an important branch artery. On one hand, difficulty of surgery is increased, and the surgery needs to be implemented by a surgeon with rich experience; and on the other hand, once positioning of the stent is not accurate during placement, or the stent is displaced during release, an important branch blood vessel may be obstructed to induce serious consequences. Furthermore, the stent is modified before surgery, and the manufacturer thereof may refuse to provide a warranty service for this reason.

A third solution is a recently proposed solution in which total aortic intraluminal intervention is performed by using a dense mesh stent. Unlike the EVAR intraluminal intervention method, this solution does not use a mechanism of mechanically obstructing a false lumen, and the dense mesh stent does not significantly hinder passage of blood flow. Instead, by forming obstruction of blood flow at an inner wall of a lesion blood vessel, hemodynamics in the false lumen are changed, the pressure in the false lumen is reduced, and intraluminal thrombus is promoted, so as to achieve the purpose of treatment. Compared with the EVAR intraluminal intervention method, since this solution uses the dense mesh stent, it not only has advantages of small trauma, fast recovery and low mortality rate, but also the dense mesh stent does not significantly obstruct delivery of blood flow to a branch artery, thereby greatly reducing difficulty of surgery. Therefore, a doctor with ordinary experience may implement this solution.

However, a treatment effect of this type of stent is not ideal enough. Since a tear of the inner wall of the blood vessel is not completely obstructed, an ideal intraluminal thrombus cannot be always formed. Furthermore, existing dense mesh stent are still difficult to be applied to all lesion types of aortic dissection and aortic aneurysm, especially difficult to be applied to type A aortic lesion.

Type A aortic dissection involves the ascending aorta, and an inner diameter of the blood vessel at this site significantly increases due to lesion, usually up to 38 mm to 55 mm. Such dense mesh stent with a large diameter cannot be radially compressed to have a very small diameter, and thus often needs a thicker delivery system. This causes placement of the delivery system through a femoral artery with a relatively small diameter to be difficult to be implemented, and even causes placement of the delivery system to be unable to be implemented especially for Asian people with relatively thinner blood vessels. In order to reduce the diameter of the stent in a compressed state, the stent may be woven by thinner wires. However, this causes a radial support force of the stent to be insufficient to achieve a therapeutic effect.

SUMMARY

In view of this, a main purpose of the disclosure is to provide a stent capable of solving or improving at least one of the above problems in the related art. Specifically, a purpose of the disclosure is to provide a stent for the treatment of aortic dissection or aortic aneurysm, especially type A aortic lesion, where a diameter of the stent in a delivery state is suitable for delivery through the femoral artery. The stent may be partially axially compressed in a release state, to form a segment with a low liquid permeability and a high radial support force at a desired site (such as a tearing site of intima of a blood vessel), and thus complete the treatment of the lesion site.

To this end, the disclosure provides a bare stent used in an aorta. The bare stent is formed by overlapping and interweaving at least two kinds of first wires and second wires with different diameters, and the bare stent has a metal coverage of at least 30% in a natural release state. Each of the first wires has a diameter of 20 μm to 150 μm, and each of the second wires has a diameter of 150 μm to 600 μm.

The bare stent of the disclosure is formed by overlapping and interweaving at least two kinds of wires with different diameters, i.e., the first wires and the second wires as defined above. The bare stent formed by interweaving the wires in the above ranges and having the above metal coverage has an appropriate radial support force in the natural release state (i.e., without axial compression and without stretch), thereby solving the problem that such a stent is difficult to be radially compressed to a delivery configuration with a suitable diameter. The stent may be radially compressed relatively easily in an appropriate range of the radial support force.

However, the radial support force of the stent of the disclosure is not sufficient to obstruct the tearing site of the intima in the aorta, and the bare stent in the natural release state still has high fluid permeability. In order to address this problem, according to a method for placing the stent as will be described in detail below, the bare stent of the disclosure is at least partially axially compressible after release. This characteristic also benefits from the bare stent of the disclosure formed by overlapping and interweaving two kinds of wires with different diameters. By way of weaving by overlapping, any wire may move in order at an intersection of a wire and another wire, which is conducive to radial compression of the bare stent. When the stent is released in the blood vessel, a sufficient weaving density is obtained in a partial segment of a non-branch blood vessel of the stent by partially axial compression, thereby significantly enhancing a radial support force and substantial liquid impermeability of the partial segment, and performing functions of expanding a true lumen of the blood vessel and obstructing a tear simultaneously at the tearing site of the intima of the blood vessel.

The stent of the disclosure needs to have a suitable metal coverage. When the weaving is too dense, it may induce difficulty in radial compression and also hinder blood flow. On the contrary, when the weaving is too sparse, even though axial compression is performed, it is difficult to achieve expected performance of the radial support force and the liquid impermeability, and thus the tearing site of the intima cannot be effectively obstructed.

According to the disclosure, the bare stent has different degrees of compression in a length direction of the bare stent when the bare stent is placed in the aorta.

In an actual application, when the bare stent of the disclosure is released in the aorta, metal coverage of different segments of the bare stent may be different from each other according to different compression ratios, for example, may vary between metal coverage in axial maximum compression and metal coverage in the natural release state.

Due to the above characteristics of the stent of the disclosure, the bare stent of the disclosure may present different radial support forces and fluid permeability according to different requirements at treatment sites, to perform multiple functions of obstructing the tear of the inner wall of the blood vessel, expanding the true lumen of the blood vessel and maintaining delivery of blood to a branch artery.

According to an embodiment, the bare stent may have a radial support force of greater than or equal to 200 N in a state in which the bare stent is naturally released in the blood vessel.

According to an embodiment, the bare stent of the disclosure may have the metal coverage of 30% to 60% and the radial support force of 200 N to 600 N in the state in which the bare stent is naturally released in the blood vessel.

According to the disclosure, the bare stent may have different degrees of compression in an axial direction of the bare stent when the bare stent is placed in the aorta.

According to an embodiment, the whole bare stent of the disclosure has a uniform braid density. To this end, the first wires are interwoven with the second wires in a uniformly distributed manner to form the bare stent.

According to an embodiment, the bare stent may have a metal coverage of greater than or equal to 80%, preferably a metal coverage of 80% to 90%, in a release and axial maximum compression state.

According to an embodiment, the bare stent may have a radial support force of greater than or equal to 400 N, preferably a radial support force of 400 N to 1000 N, in a release and axial maximum compression state.

After the bare stent is maximally compressed axially, the bare stent has a radial support force in the above range, so that it may effectively support a narrowed true lumen of the blood vessel. Therefore, in an actual application, when the stent of the disclosure is released in the blood vessel (especially the aorta), radial support forces of different segments of the stent are in fact different from each other according to compression ratios, and may vary in a range of 200 N to 1000 N.

In case that the site treated with the bare stent of the disclosure relates to an abdominal aorta site, the bare stent may be internally provided with two common iliac artery stent fixing parts configured to fix left and right common iliac artery stents. In a specific example, the common iliac artery stent fixing parts may be arranged inside the bare stent and correspond to the abdominal aorta close to a bifurcation of left and right common iliac arteries, and the two common iliac artery stent fixing parts may be configured as two annuluses tangent to each other and may be integrally formed with an inner wall of the bare stent.

Unlike fixing parts forming two cylindrical branches at a lower part of a stent for the abdominal aorta, the two fixing parts of the bare stent of the disclosure are arranged inside the bare stent, so that the exterior of the bare stent is still maintained to be cylindrical, which is more conducive to expanding the blood vessel, without causing poor support near the common iliac arteries. Furthermore, the common iliac artery fixing parts are integrally formed with the stent, so that left and right iliac artery stents may be fixed more stably.

The bare stent of the disclosure may be used in an aortic area, at least including an aortic arch and/or an abdominal aorta, from an ascending aorta to the abdominal aorta, or may be used in an aortic area, at least including an ascending aorta, from the ascending aorta to an abdominal aorta. In order to be adapted to different application sites, the bare stent of the disclosure may have different specifications. Those skilled in the art may select the specification of the bare stent according to a specific situation of the patient.

According to the disclosure, the bare stent may have the same diameter, or the bare stent may have a variable diameter, where the bare stent has the diameter ranging from 20 mm to 60 mm, preferably ranging from 20 mm to 55 mm. In general, after release, the stent should have an inner diameter slightly greater than a diameter of the blood vessel at the release site, to achieve a therapeutic effect.

According to an embodiment, the bare stent may have the diameter ranging from 20 mm to 35 mm. As to a bare stent, the entire stent may have the same diameter in the above range, or the entire stent may have a diameter variable in the above range. Such a bare stent is suitable for an aortic area from the descending aorta to the abdominal aorta and main iliac artery blood vessels of iliac arteries at both sides.

According to another embodiment, a part of the bare stent may have a diameter in a range of 38 mm to 60 mm, preferably in a range of 38 mm to 55 mm. The bare stent in a release state in the embodiment may be provided with a first segment arranged at a proximal end of the bare stent. The first segment may have a diameter of 38 mm to 55 mm to be suitable for the ascending aorta. The first segment has a length of 8 cm to 11 cm, preferably 8 cm to 10 cm after release. The stent may be further provided with a second segment adjacent to the first segment. The second segment may have a diameter of 20 mm to 35 mm for example, to be suitable for the aortic arch, even suitable for a part of the abdominal aorta. Following the first segment, the second segment extends to a distal end of the stent. The second segment may have a length of 28 cm to 40 cm, preferably 28 cm to 31 cm after release. The above two segments may also be formed into two stents respectively, and the second segment of stent partially extends into the interior of the first segment of stent upon placement. The second manner is more flexible. If necessary, three segments of independent stents may also be formed to facilitate operation.

According to other embodiments, the bare stent may have only a part corresponding to an aortic area from the descending aorta to the auxiliary aorta, and thus have a diameter of 20 mm to 35 mm and a length of 20 cm to 30 cm for example.

Each of the first wires for the bare stent of the disclosure may have a diameter of 50 μm to 150 μm, and each of the second wires may have a diameter of 150 μm to 600 μm.

According to another embodiment, the bare stent is formed by weaving three kinds of wires with different diameters, where the first wires may include at least one first thin wire and at least one second thin wire with different diameters. According to a specific embodiment, the at least one first thin wire may have a diameter of 20 μm to 100 μm, and the at least one second thin wire may have a diameter of 100 μm to 150 μm.

According to yet another embodiment, the bare stent is formed by weaving three kinds of wires with different diameters, where the second wires may include at least one first thick wire and at least one second thick wire with different diameters. According to a specific embodiment, the at least one first thick wire may have a diameter of 150 μm to 300 μm, and the at least one second thick wire may have a diameter of 300 μm to 600 μm.

According to still another embodiment, the bare stent is formed by weaving four kinds of wires with different diameters, i.e., the first thin wire and the second thin wire as well as the first thick wire and the second thick wire.

Certainly, more kinds of wires with different diameters may be used, however, the cost performance of such an arrangement is low taking the effect and the cost into account.

The number of wires for weaving the bare stent may range from 48 to 156, preferably from 48 to 128. Here the number of the second wires may be 4 or more, such as 4 to 32, and the remaining wires form the first wires.

According to an embodiment, the number of wires for weaving the bare stent may range from 48 to 156, here the number of the second wires ranges from 4 to 32, and the remaining wires form the first wires. The first wires may include 32 to 120 first thin wires and 32 to 120 second thin wires, provided that a sum of the number of the first thin wires and the number of the second thin wires is less than or equal to 152.

According to another embodiment, the number of wires for weaving the bare stent may range from 48 to 156, here the second wires include 6 to 24 first thick wires and 6 to 24 second thick wires, and the remaining wires form the first wires, provided that a sum of the number of the first thick wires and the number of the second thick wires is less than or equal to 32.

In case of too much number of thick wires (i.e., the second wires), the stent cannot be effectively compressed into an ideal delivery state, while in case of too small number of thick wires, the stent cannot provide an expected radial support force even after the stent is compressed, and an expected structure and morphology of the stent cannot be maintained in a release state. In particular, as for the bare stent of the disclosure, the number of the second wires preferably is less than or equal to 30, preferably is less than or equal to 24.

According to an embodiment, the bare stent may be formed of at least two layers of woven meshes. According to an embodiment, the bare stent may be provided with two, three or four layers of woven meshes, preferably two layers of woven meshes. When the bare stent is provided with multiple layers of woven meshes, the stent has the radial support force and the metal coverage as specified above.

It should be understood that according to a range of the radial support force and a range of the metal coverage required for a specific treatment type, those skilled in the art may select a suitable woven material and determine a reasonable number of layers under specific device conditions according to descriptions here, further select a suitable diameter, number, or the like of the wire, and determine a suitable weaving solution to obtain a stent having the required range of the radial support force and the required range of the metal coverage. For example, a suitable weaving solution may be designed by a dedicated software.

According to a further embodiment, an end (especially the proximal end where the stent has a maximum radial support force) of the bare stent of the disclosure may be formed in a return weaving manner. As for another end of the bare stent, if there is a burr which cannot be woven again in a return weaving manner, the burr may be located on an inner side of the bare stent by selecting a suitable arrangement of the layers; or if there are two layers of burrs, the burr at one layer of the two layers is woven in a return weaving manner by a short segment, and the other burr is wrapped in said segment which is woven in a return weaving manner, or when multiple stents are used in cooperation, burrs at a single layer or two layers may be overlapped with each other and placed in another dense mesh stent. The bare stent according to the embodiment has a smooth end, thereby avoiding mechanical damage to the inner wall of the blood vessel by an exposed end (burr) of the wire.

The bare stent of the disclosure is self-expandable or capsular expandable. Materials of the first wires and materials of the second wires for weaving the bare stent may be different from each other, however, preferably the same. Usually, the materials of the wires may be metal, such as shape memory alloy (e.g., nitinol), cobalt-chromium alloy, tungsten, or tantalum.

The bare stent of the disclosure may be delivered through a femoral artery by using a delivery system with a conventional outer diameter (e.g., about 5 mm to about 10 mm, preferably about 5 mm to about 7 mm), without usage of a delivery system with a larger outer diameter.

DETAILED DESCRIPTION

Figure 1:
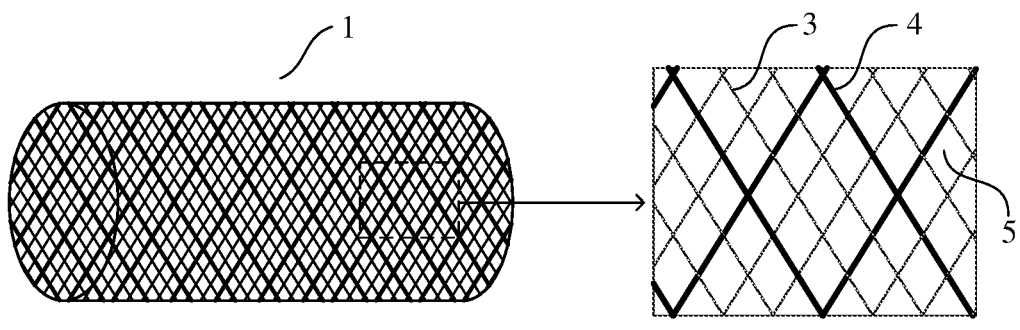
FIG. 1 is a schematic view and schematic partially enlarged view of a stent according to the disclosure.

Technical solutions in embodiments of the disclosure will be clearly and completely described below in combination with the embodiments of the disclosure and the drawings. It is apparent that the described embodiments are only part of the embodiments of the disclosure, rather than all the embodiments, and the technical solutions recited in the embodiments of the disclosure may be implemented in any combination without conflict. All other embodiments obtained by those of ordinary skill in the art based on the embodiments of the disclosure without paying any creative work belong to the scope of protection of the disclosure.

Throughout the description, terms used here should be understood as meanings as usually used in the art, unless specifically stated otherwise. Therefore, unless defined otherwise, all technical and scientific terms used here have same meanings as usually understood by those skilled in the art to which the disclosure belongs. When there is a contradiction, meanings of the description are preferred.

Like reference numerals in the drawings refer to like components. Shapes and dimensions of components in schematic drawings are for illustration only and cannot be considered to reflect actual shapes, dimensions and absolute positions.

It should be noted that in the disclosure, terms "including", "include", or any other variants thereof are intended to cover a non-exclusive inclusion, so that a method or device including a series of elements not only includes elements which are explicitly recited, but also includes other elements which are not explicitly listed, or further includes elements inherent to implementation of the method or device.

It should be noted that terms "first\second" involved in the disclosure are only intended to distinguish similar objects, and do not represent a specific sequence of the objects, and it may be understood that "first\second" may exchange a specific sequence or order in an allowable situation. It should be understood that objects distinguished by "first\second" may be interchanged in an appropriate situation, to enable embodiments and examples of the disclosure described here to be implemented in an order other than those illustrated or described here.

In order to describe the disclosure more clearly, terms "proximal end" and "distal end" are customary terms in the field of intervention medical treatment. Here "distal end" represents an end away from the heart during surgical operation, and "proximal end" represents an end close to the heart during surgical operation.

In the disclosure, unless stated otherwise, terms "bare stent" and "stent" may be used interchangeably and have the same meaning, that is, they refer to a bare stent.

The disclosure provides a bare stent used in an aorta, the bare stent is formed by weaving at least two kinds of first wires and second wires with different diameters, and the stent is configured to be at least partially compressible along an axial direction of the stent in a release state.

FIG. 1 shows a schematic view and schematic partially enlarged view of a stent 1 according to the disclosure. The stent 1 is formed by overlapping and weaving multiple first wires 3 and multiple second wires 4. The stent 1 shown in FIG. 1 is a single-layer mesh structure with meshes 5.

The stent of the disclosure may also be a structure with multiple layers, such as 2 to 4 layers. For example, the multiple layers may be formed in a return weaving manner.

The stent of the disclosure is suitable for any segment from the ascending aorta to the abdominal aorta or even the whole aorta. Therefore, the stent of the disclosure may have a large diameter ranging from about 60 mm to about 20 mm (preferably, ranging from 55 mm to about 20 mm).

According to the disclosure, the stent 1 may be formed by weaving a total of 48 to 156 wires, preferably 48 to 128 wires. For example, by way of enumeration, the stent of the disclosure may be formed by weaving 48, 64, 96, 128 wires. The number of the wires may be determined according to the diameter of the stent, the number of layers, materials of the used wires, or the like.

Material for the stent of the disclosure may be any material suitable for a peripheral vascular stent, as long as the material may provide a sufficient radial support force and have a certain fineness. Usually, metal wires such as nickel-titanium alloy wires, cobalt-chromium alloy wires, tungsten wires, tantalum wires, or the like are preferably used, and nickel-titanium alloy wires are preferred.

There are at least four second wires 4 serving as thick wires, and usually the number of the second wires 4 is less than or equal to 32. The diameter of each second wire 4 is included between 150 μm and 600 μm, and for example, the diameter of each second wire 4 is 150 μm, 200 μm, 250 μm, 300 μm, 350 μm, 400 μm, 450 μm, 500 μm, 550 μm, or 600 μm. The second wires 4 provide a basic support force and a complete structure for the stent 1. However, the number of the second wires cannot be too much. For example, even though wires with the diameter of only 300 μm are used, when about 32 wires are used, the stent is difficult to be compressed to a suitable delivery dimension and thus is unable to use, especially for a stent part with ultra-large diameter greater than about 40 mm.

In the stent 1, the remaining wires except the thick wires are first wires 3 serving as thin wires. Each first wire 3 of the disclosure may have a diameter of 20 μm to 150 μm, preferably a diameter of 50 μm to 150 μm, such as 50 μm, 60 μm, 70 μm, 80 μm, 90 μm, 100 μm, 110 μm, 1120 μm, 130 μm, 140 μm and 150 μm. The first wires 3 perform functions of auxiliary supporting the stent 1 and filling gaps between the second wires 4. Furthermore, the first wires 3 also perform a function of maintaining the shape of the stent 1, since the number of the first wires is much greater than the number of the second wires 4. The inventors have found that although it seems to be feasible theoretically, in fact, when the overlapping and weaving manner of the disclosure is used, a large-diameter stent with a certain shape and a sufficient support force cannot be formed by second wires (i.e., thick wires) alone. Furthermore, even if diameters of the wires are the same, a large-diameter stent with a fixed wire-to-wire intersection formed by using for example a laser engraving technology has a much smaller support force, which cannot achieve requirements for aortic blood vessels according to the disclosure.

The stent 1 of the disclosure is formed by interweaving in an overlapping manner, and a free relative movement may be generated at an intersection between the wires, so that any mesh 5 on the stent 1 of the disclosure may be easily compressed. Therefore, in case that an end of the stent 1 formed as such is fixed, the stent 1 may be axially compressed along a central axis A-A of the stent into a compressed stent 1', or the stent 1 may be radially compressed along a D-D direction toward the central axis of the stent into a compressed stent 1" (see FIG. 2).

The expression "interleaving" as mentioned here refers to forming the stent by always weaving the first wires and the second wires together from an end to another end of the stent, to distinguish from those weaving manners in which one segment of a stent including multiple segments is woven by wires with one diameter and another segment is woven by wires with another diameter.

Figure 2:
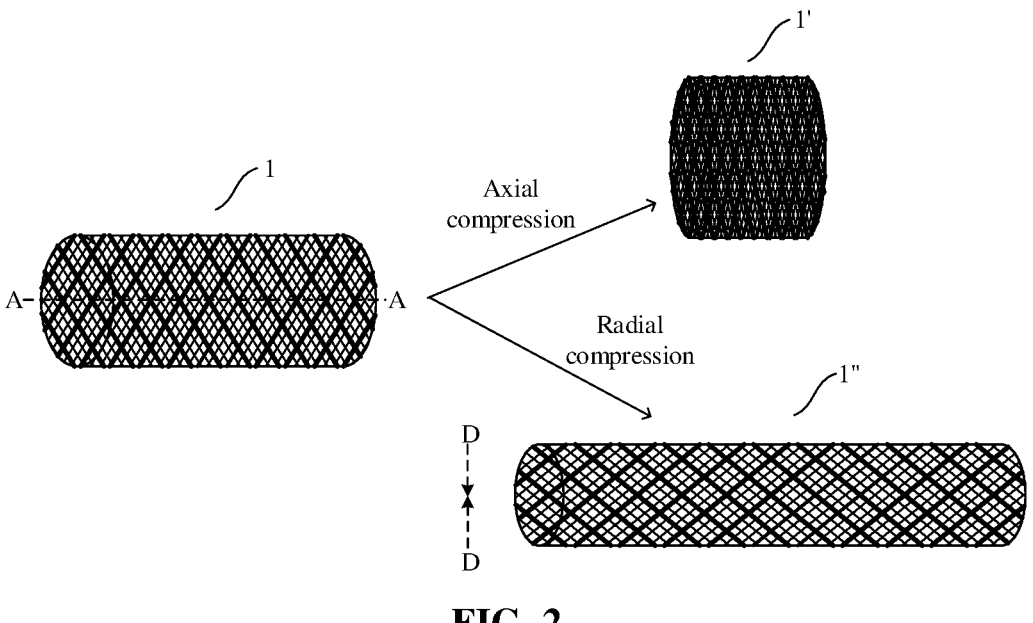
FIG. 2 is a schematic view illustrating partially axial compression and stretching of a stent according to the disclosure.

The expression "axial direction" of the stent as mentioned here refers to a direction along A-A as shown in FIG. 2, which is a direction of a central axis of a cylindrical shape of the stent. The expression "radial direction" of the stent as mentioned here refers to a direction along D-D as shown in FIG. 1, which is a diameter direction of a circle of the cylindrical shape of the stent. In general, "radially compressed" here refers to compression in a direction from the circumference to the center of the circle.

The above characteristics of the stent of the disclosure may bring many benefits. Since the stent may be axially compressed, the compressed stent forms a high radial support force and a high braid coverage. The high radial support force may achieve effective expansion of a narrowed part of the blood vessel, and the high braid coverage may achieve very low fluid permeability and effectively obstruct rupture of the intima of the blood vessel. At this time, the second wires 4 in the stent 1 perform a function of a support skeleton, and the first wires fill the gaps between second wires to achieve a function of a fabric film similar to the covered stent. Unlike the covered stent, the bare stent of the disclosure may provide a relatively high radial support force after subject to axial compression, and even may be effectively used in the treatment of type A aortic dissection involving the ascending aorta.

The stent 1 of the disclosure may have a radial support force of greater than or equal to 200 N in a natural release state, and may have a radial support force of greater than or equal to 400 N in an axial maximum compression state.

The expression "natural release state" of the stent as mentioned here refers to a state in which the stent is not axially compressed and is released, when it is fixed in a water bath at 37±2° C.

The expression "axial maximum compression state" of the stent as mentioned here refers to a state in which the stent is axially compressed until it is unable to be further compressed, when it is in the natural release state.

The expression "radial support force" of the stent as mentioned here refers to a force required to compress the stent along a diameter direction to have 85% of its original diameter, after it is fixed in the natural release state.

Along with the radial support force, the stent of the disclosure also requires a high liquid permeability to obtain an effect of effectively obstructing a tear of the intima of the blood vessel. This property may be represented by metal coverage. The stent 1 of the disclosure may have a metal coverage of 30% to 60% in the natural release state, and may have a metal coverage of greater than or equal to 80% in the axial maximum compression state.

The expression "metal coverage" of the stent as mentioned here refers to a metal coverage ratio per unit area, which is measured by electron microscope scanning. A sum of the metal coverage and a void ratio per unit area should be 100%.

Figure 3:
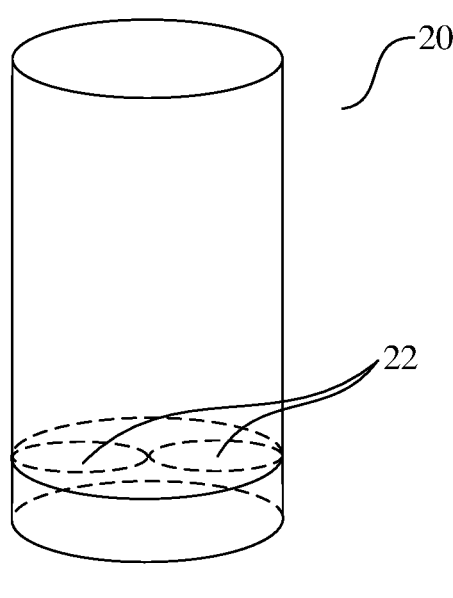
FIG. 3 is a schematic view of a bare stent according to another embodiment of the disclosure.

FIG. 3 shows a variant embodiment of the disclosure. According to the embodiment, at a part of the bare stent corresponding to the abdominal aorta which is the treatment site, the bare stent of the disclosure may be provided with two common iliac artery stent fixing parts configured to receive and fix left and right common iliac artery stents. With reference to FIG. 3, a bare stent of the embodiment is schematically shown. The stent 20 shown in FIG. 3 is suitable for a segment of the abdominal aorta. Common iliac artery stent fixing parts 22 arranged as two adjacent annular channels are provided at interior of a lower part of the stent 20. For the sake of clarity, each fixing part 22 is shown as a plane in FIG. 3, and in fact, each fixing part 22 has a certain thickness. In some examples, each common iliac artery stent fixing part 22 may extend downward to a lower end of the stent 20.

Each common iliac artery stent fixing part 22 is also formed by weaving the same first and second wires as the stent 20 (the first and second wires are not shown), and is integrally formed with the bare stent. Outer parts of the two annular channels are integrally woven with an inner wall of the stent 20. The dimensions of inner diameters of the two annular channels are adapted to outer diameters of the left and right common iliac artery stents to be received and fixed, and are usually slightly less than the outer diameters of the left and right common iliac artery stents, so as to be able to fix the common iliac artery stents.

Figure 4:
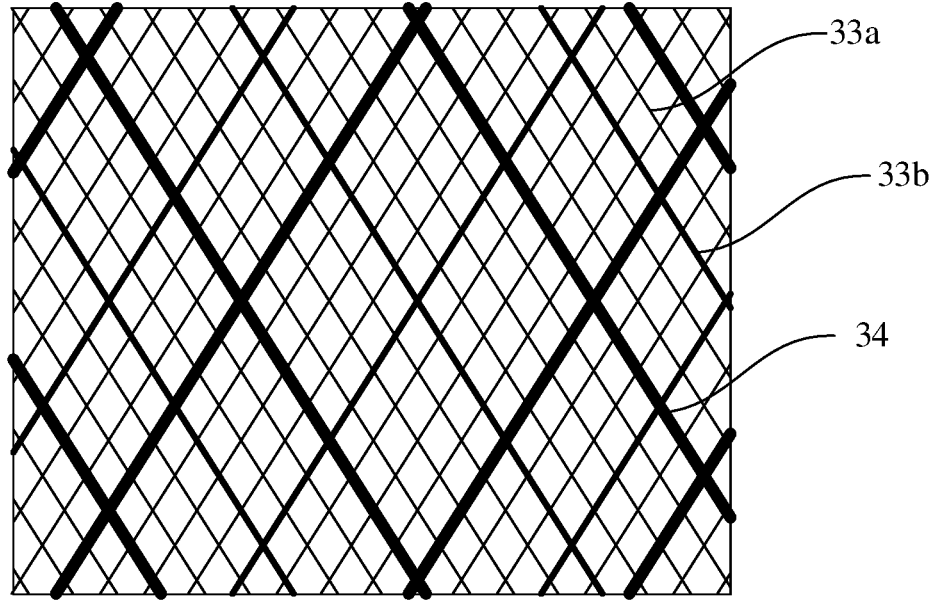
FIG. 4 is a schematic partially enlarged view of a stent according to an embodiment of the disclosure.

According to an embodiment, the stent of the disclosure may be formed by weaving three kinds of wires with different diameters. As shown in FIG. 4, a schematic partially enlarged view of a single layer of the stent of the embodiment is shown. The stent is formed by weaving two kinds of first wires 33a, 33b and a kind of second wire 34. Here the first wires include a first thin wire 33a which may have a diameter of 50 μm to 100 μm, and a second thin wire 33b which may have a diameter of 100 μm to 150 μm. The second wire may have a diameter of 150 μm to 600 μm, preferably a diameter of 150 μm to 400 μm. The embodiment may also have other variations. For example, the stent (not shown) is formed by a kind of first wire and two kinds of second wires (for example, their diameters are in a range of 150 μm to 300 μm and a range of 300 μm to 600 μm, respectively), or formed by two kinds of first wires and two kinds of second wires, but is not limited thereto.

A radial support force of the stent formed by three or more kinds of wires with different diameters is more uniform in the whole stent, and flexibility of the stent may also be enhanced.

Figure 5:
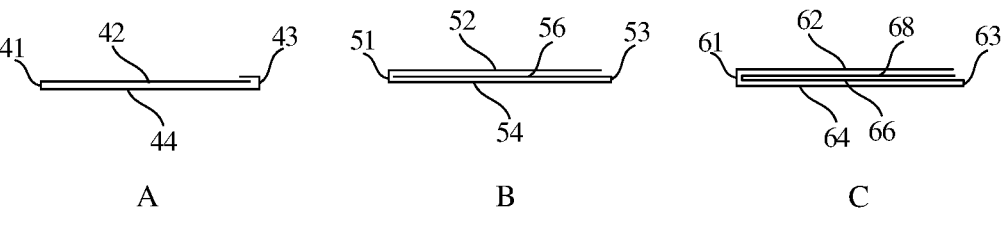
FIG. 5 is a schematic cross-section view of a wall of a stent with multiple layers according to the disclosure.

As described above, the stent of the disclosure may be provided with multiple layers, preferably two layers, three layers, or four layers. According to a preferred embodiment, the stent with multiple layers may be formed by weaving a single-layer woven mesh in a return weaving manner. As shown in the parts A to C of FIG. 5, schematic cross-section views of walls of stents with two to four layers are shown. The part A of FIG. 5 shows a structure with two layers, and in this figure, an upper layer 42 of the structure is located at a side of the stent close to the interior of the stent, and a lower layer 44 of the structure is located at a side of the stent close to exterior (i.e., a side in contact with the wall of the blood vessel) of the stent. A smooth port is formed at a proximal end 41 of the structure due to the return weaving. At a distal end 43 of the structure, the lower layer 44 facing toward the exterior of the stent is woven in a return weaving manner by a certain distance, to wrap, inside the lower layer 44, an opened edge (burr) of a distal end of the upper layer 42 facing toward the interior of the stent. Thus, a port with both smooth ends is formed. Similarly, in the part B of FIG. 5, an upper layer 52 is woven at a proximal end 51 in a return weaving manner to form a lower layer 54 and is further woven at a distal end 53 in a return weaving manner to form an intermediate layer 56. At the distal end 53, the lower layer 54 and the intermediate layer 56 are slightly longer than the upper layer 52, so that an opened edge of a distal end of the upper layer is located inside the stent. In this way, both ends of the stent are also smooth ports. The same principle is also applied to four layers in the part C of FIG. 5. At a distal end 63, two layers 62, 68 close to the interior of the stent are shorter than an edge formed by weaving two layers 64, 66 close to the exterior of the stent in a return weaving manner, while a proximal end 61 forms a lowermost layer 64 by weaving an uppermost layer 62 in a return weaving manner, to wrap two intermediate layers 68 and 66 therebetween. A variation may be possible that a distal end of the uppermost layer 62 or intermediate layer 68 is woven in a return weaving manner by a small segment, to wrap an opened edge of another layer. In this way, both ends of the stent are completely smooth ports.

Preferably, the stent of the disclosure is in the form of multiple layers, so that both ends (especially the proximal end) of the stent may form smooth ports, avoiding secondary damage to the blood vessel by an opened edge of the braid.

The stent of the disclosure is described in detail as above by way of examples. It should be understood by those skilled in the art that the above examples are intended to explain advantages of the stent of the disclosure, rather than limiting the scope of the disclosure, and features in an example may be applied to the stent of another example separately or in combination in an appropriate situation. Apparent variations and modifications made to the stent by those skilled in the art according to contents of the disclosure here fall within the scope of the disclosure, as long as they meet the concept of the disclosure.

The stent of the disclosure may be placed at a respective site of the blood vessel by a stent delivery system. The delivery system which may be configured to deliver the stent of the disclosure has an outer diameter suitable for placement of a conventional aortic stent, for example 5 cm to 10 cm, preferably 5 cm to 7 cm. The stent as described above in the disclosure is assembled in the system in a delivery configuration, both ends of the stent are constrained, and the constraints are removed only after other parts of the stent are released, so that the stent is completely released.

Figure 6:
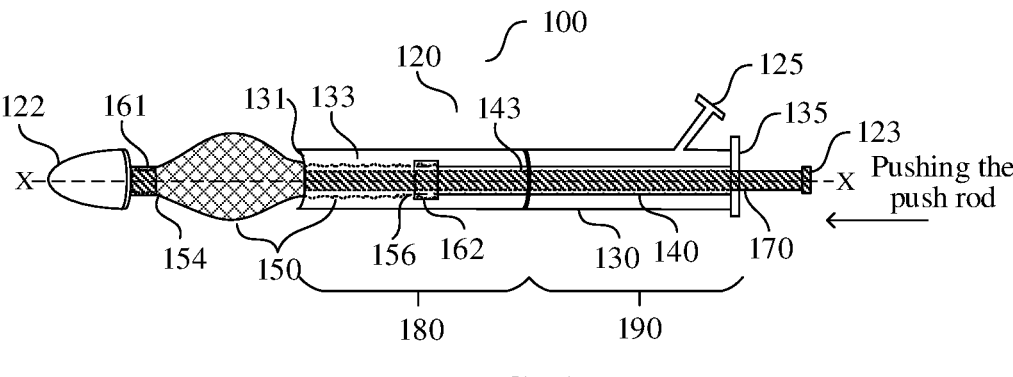
FIG. 6 is a schematic view of a stent delivery system according to the disclosure.

With reference to FIG. 6, a schematic view of a stent delivery system 100 according to the disclosure is shown. A stent delivery catheter 120 includes an outer catheter 130, an inner catheter 140 and a push rod 170 which are coaxially arranged sequentially from exterior to interior along a longitudinal axis X-X. The delivery catheter 120 is provided with a distal end 123 and a proximal end 122. The delivery catheter 120 is further provided with a hemostatic valve 125.

The outer catheter 130 is provided with a proximal end 180 and a distal end 190, and a first hollow cavity 133 penetrates through the whole outer catheter 130. The inner catheter 140 is arranged coaxially with the outer catheter 130 along the longitudinal axis X-X in the first hollow cavity 133 at the distal end 190 of the outer catheter, and the inner catheter 140 is provided with a second hollow cavity 143. The push rod 170 extends through the first hollow cavity 133 of the outer catheter 130 and extends through the second hollow cavity 143 of the inner catheter 140, until extending beyond a port 135 of the distal end of the outer catheter. The push rod 170 may be provided with a third hollow cavity (not shown) for the passage of guide wires.

At the proximal end 180 of the outer catheter 130, the stent 150 is releasably maintained in the first hollow cavity 133 between the push rod 170 and the outer catheter 130 in a delivery configuration. A proximal end 154 of the stent 150 is constrained at a proximal end of the push rod 170 by a first constraint component 161. The first constraint component 161 may be a conventional stopper which may be removed from the stent 150 if necessary, to release the proximal end 154 of the stent 150. A distal end 156 of the stent 150 is constrained at a proximal end of the inner catheter 140 by a second constraint component 162. Similarly, the second constraint component 162 may be a conventional stopper which may be removed from the stent 150 if necessary, to release the distal end 156 of the stent 150.

According to the delivery system 100 of the embodiment, a proximal end 131 of the outer catheter 130 may be separated from the proximal end 122 of the delivery catheter 120, and relative movement may occur among the outer catheter 130, the inner catheter 140 and the push rod 170 by pushing the push rod 170 toward the proximal end or by pulling the outer catheter 130 toward the distal end.

According to the system 100 shown in FIG. 6, by pushing the push rod 170 toward the proximal end 122, the proximal end 122 of the delivery catheter 120 drives the push rod 170 fixedly connected to the proximal end 122, the stent 150 constrained together with an end of the push rod 170 and the inner catheter constrained together with the distal end of the stent to move toward the proximal end relative to the outer catheter 130. In this way, the stent 150 is started to be released from the proximal end 154 thereof.

Figure 7:
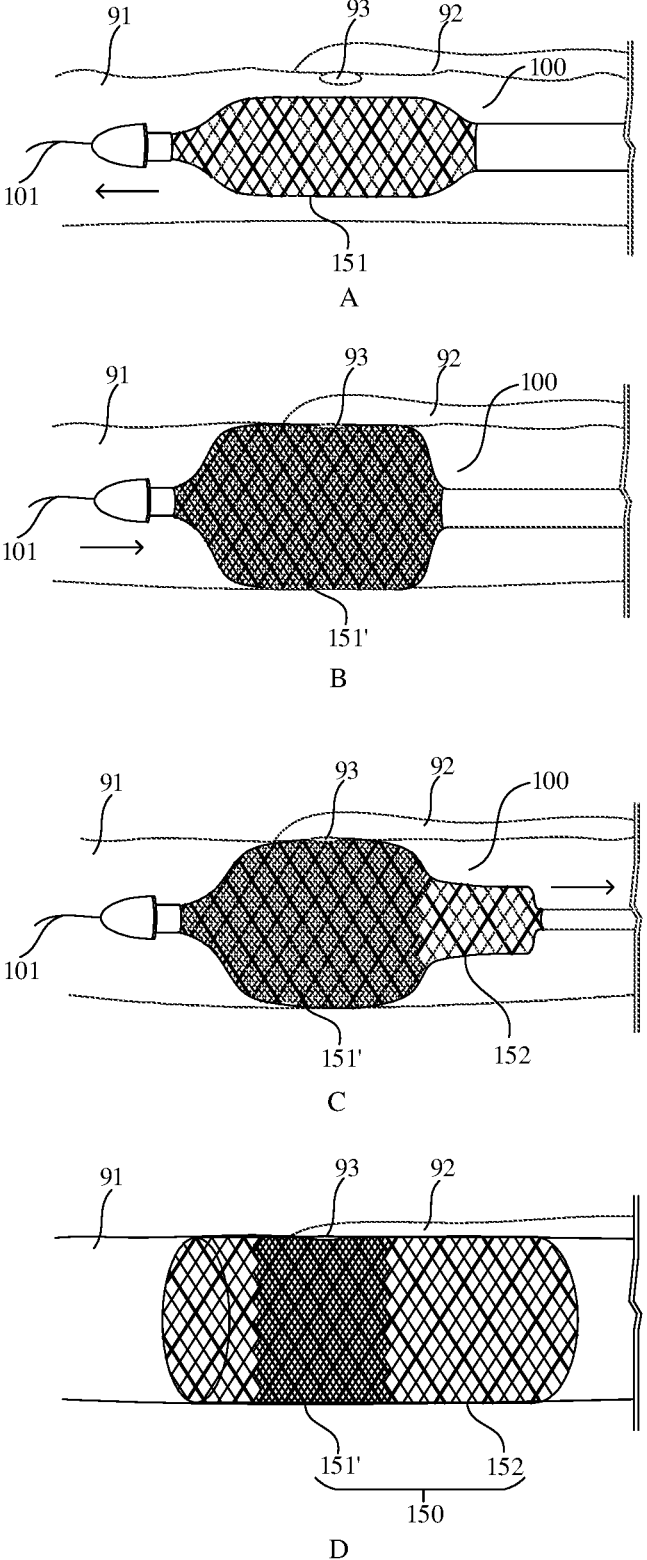
FIG. 7 is a schematic view illustrating placing a stent at a tear of intima of an aorta by using a stent delivery system of the disclosure.

With reference to FIG. 7, a schematic view illustrating placing a stent at a tear of intima of an aorta by using the stent delivery system of the disclosure is shown. The part A of FIG. 7 shows a segment of aortic blood vessel 91 including a tear 93 of an intima of the blood vessel, and tearing of the intima is induced by the tear 93 to form a false lumen 92. The stent delivery system 100 of the disclosure has been guided to the tear 93, and has released a segment 151 of the stent by pushing the push rod in a direction indicated by the arrow in case that the position of the outer catheter 130 remains unchanged. With further reference to the part B of FIG. 7, the position of the inner catheter and the position of the outer catheter of the delivery system 100 remain unchanged, and the push rod is pulled back in a direction indicated by the arrow in this figure, so that the released segment 151 of the stent is compressed back and finally abuts against a blood vessel area in which the tear 93 of the intima of the blood vessel is located, to form a compressed segment 151'. When the stent is designed, the diameter of the stent is usually designed to be slightly greater than the diameter of the blood vessel at a placement site. Therefore, the compressed segment 151' tightly abuts against an inner wall of this segment of the blood vessel, obstructs the tear 93, and expands a true lumen of this segment of the blood vessel. The compressed segment 151' is remained in this segment of the blood vessel with the compressed shape due to an inward contraction force caused by the wall of the blood vessel.

Next, as shown in the part C of FIG. 7, the remaining segment 152 of the stent is further released by pulling the outer catheter 130 toward the distal end in a direction indicated by the arrow in this figure (the inner catheter 140 and the push rod 170 remain stationary). Finally, after the stent 150 is completely released, constraints of the stoppers on both ends of the stent are removed, so that the whole stent 150 is released to the treatment site, and the delivery catheter is withdrawn from the blood vessel (see the part D of FIG. 7). The stent 150 placed at a lesion site is provided with two segments, one of which is the compressed segment 151', and the other of which is a natural release segment 152. The compressed segment 151' performs functions of obstructing the tear 93 and forming relatively strong radial support on the blood vessel. The natural release segment 152 performs a function of supporting other parts of the blood vessel appropriately, and does not hinder flow of blood, in particular flow of blood toward a branch blood vessel.

According to the disclosure, after the segment 151 of the stent is released (i.e., a state shown in the part A of FIG. 7), the position of the stent may be confirmed, so that the tear 93 may be accurately obstructed by the compressed segment. If said position is not ideal enough, adjustment may be performed, and even the released segment 151 is retracted into the outer catheter again. The stent is released again after the position of the delivery system is adjusted.

Similarly, the position of the stent may be confirmed after any segment of the stent is released, to achieve a best placement effect. Finally, the position of the stent is confirmed again before constraints on both ends of the stent are removed, since the stent may be retracted and released again when it is found that its placement position is not ideal at this time. After constraints on both ends of the stent are removed, the position of the stent cannot be adjusted.

Furthermore, other segments of the stent are compressed in a manner similar to that shown in the part B of FIG. 7. For example, when a front part of the stent is released and has abutted against the wall of the blood vessel, a segment of the stent continues to be released. Since a subsequently released end of the stent is constrained by the outer catheter, by remaining the push rod stationary and simultaneously moving the outer catheter and the inner catheter toward the proximal end, a segment, which is newly released but has not yet abutted against the wall of the blood vessel, of the stent is compressed and abuts against the wall of the blood vessel, to form a segment with a high metal coverage and a high radial support force.

Detailed solutions of the stent delivery system of the disclosure and the method for placing the stent into the blood vessel by using the system are explained by the above examples. Variations and modifications may be readily made by those skilled in the art based on the above contents, to be adapted to actual application requirements without departing from the spirit of the disclosure. These variations and modifications also fall within the scope of the disclosure.

Embodiment

The embodiment provides a bare stent with a structure similar to that shown in FIG. 1, and the stent is used in an area of the descending aorta. The bare stent is made of a nickel-titanium alloy material, and is formed by interweaving 54 first wires with 12 second wires, where each of the 54 first wires has a diameter of 100 μm, and each of the 12 second wires has a diameter of 400 μm. The bare stent is woven into two layers in a return weaving manner. The return weaving manner is shown in the part A of FIG. 5, where the proximal end is a smooth end which is woven in a return weaving manner, and the distal end includes two layers of burrs. A blur edge at the outer side is woven in a return weaving manner by a short segment, to place a blur edge at the inner side inside said segment which is woven in a return weaving manner, to prevent the burr from being exposed, which damages the wall of the blood vessel.

The bare stent has a conical shape, the diameter of the proximal end of the bare stent is 45 mm, the diameter of the distal end of the bare stent is 32 mm, and the length of the bare stent is 8 cm. A fixed length of the stent after it is released in the blood vessel may reach 24 cm.

By scanning electron microscope detection, the stent of the embodiment has a metal coverage of 40% in a natural state, and the stent has a metal coverage of about 90% after axial maximum compression. As detected by a radial support force tester, a radial support force of a thicker part of the stent of the embodiment is 350 N in the natural state, and a radial support force of each part of the stent is greater than 400 N, even greater than 600 N after the axial maximum compression.

Furthermore, in order to simulate a situation of axial bending stress of the stent when the stent is fixed at the aortic arch, a radial return force of the stent is measured to be 0.4 N to 1.0 N.

The forgoing is only part of specific embodiments of the disclosure, and thus is not intended to limit the scope of the disclosure. Any equivalent structural transformation made by using the description and drawings of the disclosure within the inventive concept of the disclosure, or directly/indirectly applied to other related technical fields is included within the patent scope of protection of the disclosure.

What is claimed is:

1. An axially compressible bare stent, wherein the bare stent is configured to be used in an aorta, the bare stent being formed by overlapping and interweaving at least two kinds of wires with different diameters, the at least two kinds of wires comprising first wires and second wires, and the bare stent having a metal coverage of at least 30% in a natural release state, wherein each of the first wires has a diameter of 20 μm to 150 μm, and each of the second wires has a diameter of 150 μm to 600 μm, wherein the first wires comprise at least one first thin wire and at least one second thin wire with different diameters, and wherein the at least one first thin wire has a diameter of 20 μm to 100 μm, and the at least one second thin wire has a diameter of 100 μm to 150 μm, wherein the bare stent is formed by weaving 48 to 156 wires, wherein 4 to 32 wires of the 48 to 156 wires form the second wires, and remaining wires of the 48 to 156 wires form the first wires, and wherein the first wires comprises 32 to 120 first thin wires and 32 to 120 second thin wires, provided that a sum of a number of the first thin wires and a number of the second thin wires is less than or equal to 152.

2. The axially compressible bare stent of claim 1, wherein the bare stent has a radial support force of greater than or equal to 200 N in the natural release state.

3. The axially compressible bare stent of claim 2, wherein the bare stent has the metal coverage of 30% to 60% and the radial support force of 200 N to 600 N in the natural release state.

4. The axially compressible bare stent of claim 2, wherein the first wires are interwoven with the second wires in a uniformly distributed manner to form the bare stent.

5. The axially compressible bare stent of claim 1, wherein the bare stent has different degrees of compression in an axial direction of the bare stent when the bare stent is configured to be placed in the aorta.

6. The axially compressible bare stent of claim 1, wherein the bare stent has a metal coverage of greater than or equal to 80% in a release and axial maximum compression state.

7. The axially compressible bare stent of claim 1, wherein the bare stent has a metal coverage of 80% to 90% in a release and axial maximum compression state.

8. The axially compressible bare stent of claim 1, wherein the bare stent has a radial support force of greater than or equal to 400 N in a release and axial maximum compression state.

9. The axially compressible bare stent of claim 8, wherein the bare stent has the radial support force of 400 N to 1000 N in the release and axial maximum compression state.

10. The axially compressible bare stent of claim 1, wherein the bare stent is configured to be used in an area comprising an abdominal aorta, and the bare stent is internally provided with two common iliac artery stent fixing parts configured to fix left and right common iliac artery stents.

11. The axially compressible bare stent of claim 10, wherein the two common iliac artery stent fixing parts are arranged inside the bare stent and correspond to the abdominal aorta close to a bifurcation of left and right common iliac arteries, and wherein the two common iliac artery stent fixing parts are a configured as two annuluses tangent to each other and are integrally formed with an inner wall of the bare stent.

12. The axially compressible bare stent of claim 1, wherein the bare stent has a same diameter in an axial direction of the bare stent, or the bare stent has a variable diameter in an axial direction of the bare stent, wherein the bare stent has the diameter ranging from 20 mm to 60 mm.

13. The axially compressible bare stent of claim 12, wherein the bare stent has the diameter ranging from 20 mm to 35 mm.

14. The axially compressible bare stent of claim 12, wherein a part of the bare stent has a diameter ranging from 38 mm to 60 mm.

15. The axially compressible bare stent of claim 1, wherein the bare stent is provided with at least two layers of woven meshes.

16. An axially compressible bare stent, wherein the bare stent is configured to be used in an aorta, the bare stent being formed by overlapping and interweaving at least two kinds of wires with different diameters, the at least two kinds of wires comprising first wires and second wires, and the bare stent having a metal coverage of at least 30% in a natural release state, wherein each of the first wires has a diameter of 20 μm to 150 μm, and each of the second wires has a diameter of 150 μm to 600 μm, wherein the second wires comprise at least one first thick wire and at least one second thick wire with different diameters, and wherein the at least one first thick wire has a diameter of 150 μm to 300 μm, and the at least one second thick wire has a diameter of 300 μm to 600 μm, wherein the bare stent is formed by weaving 48 to 128 wires, wherein 6 to 24 first thick wires and 6 to 24 second thick wires of the 48 to 128 wires form the second wires, and remaining wires of the 48 to 128 wires form the first wires, provided that a sum of a number of the first thick wires and a number of the second thick wires is less than or equal to 32.

\* \* \* \* \*